(12) United States Patent
Alpert et al.

(10) Patent No.: US 6,499,357 B2
(45) Date of Patent: Dec. 31, 2002

(54) HEAT FLUX MEASUREMENT PIPE AND METHOD FOR DETERMINING SPRINKLER WATER DELIVERY REQUIREMENT

(75) Inventors: Ronald L. Alpert, Sharon, MA (US); John L. de Ris, Foxborough, MA (US); Lawrence Orloff, Foxboro, MA (US)

(73) Assignee: Factory Mutual Research Corporation, Norwood, MA (US)

( * ) Notice: Subject to any disclaimer, the term of this patent is extended or adjusted under 35 U.S.C. 154(b) by 0 days.

(21) Appl. No.: 09/804,075

(22) Filed: Mar. 13, 2001

(65) Prior Publication Data

US 2002/0152818 A1 Oct. 24, 2002

(51) Int. Cl.[7] .............................................. G01F 1/100
(52) U.S. Cl. ....................................................... 73/861
(58) Field of Search ..................... 73/861, 193; 374/16, 374/37; 165/33, 275; 261/130

(56) References Cited

U.S. PATENT DOCUMENTS

| | | | |
|---|---|---|---|
| 2,329,813 A | | 9/1943 | Amsler |
| 3,167,957 A | | 2/1965 | Ziviani |
| 3,580,070 A | | 5/1971 | Cumpston |
| 3,712,131 A | * | 1/1973 | Smith ........................... 73/190 |
| 4,812,051 A | | 3/1989 | Paulik et al. |
| 4,925,314 A | | 5/1990 | Claudy et al. |
| 4,926,356 A | | 5/1990 | Kucera et al. |
| 5,315,292 A | * | 5/1994 | Prior ........................... 340/628 |
| 5,940,784 A | | 8/1999 | El-Husayni |
| 6,085,585 A | * | 7/2000 | Yu et al. ........................ 73/168 |
| 6,121,882 A | * | 9/2000 | Jaul et al. ..................... 340/584 |
| 6,158,476 A | * | 12/2000 | Sjotun ........................ 138/126 |

* cited by examiner

Primary Examiner—Benjamin R. Fuller
Assistant Examiner—Jewel V. Thompson
(74) Attorney, Agent, or Firm—Venable; John P. Shannon; Chad C. Anderson

(57) ABSTRACT

A method of evaluating fire hazards of materials in standard tests is provided which comprises measuring heat flux distribution in test fires at the moment when sprinklers would have sensed the fire and be activated, and determining the rate of sprinkler water delivery rate that will absorb the heat flux, thus controlling spread of the fire.

9 Claims, 5 Drawing Sheets

Fig. 1

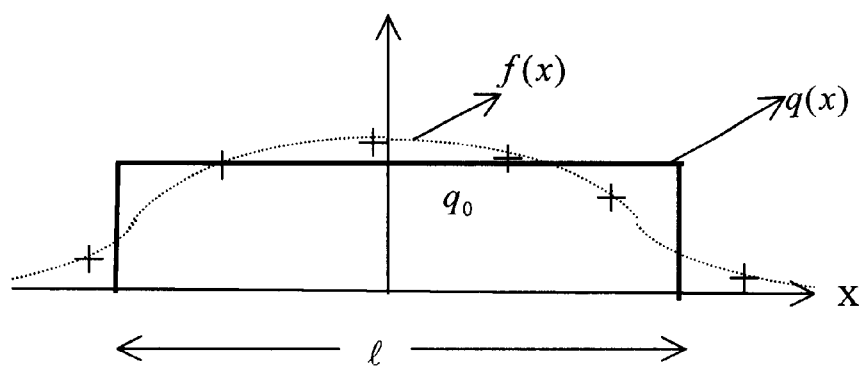
Fig. 6 Determination of Effective Heat flux, $q_0$, and length, $\ell$, of a Measured Heat Flux Distribution, $f(x)$.

HEAT FLUX MEASUREMENT PIPE AND METHOD FOR DETERMINING SPRINKLER WATER DELIVERY REQUIREMENT

BACKGROUND OF THE INVENTION

1. Field of the Invention

The invention relates to a method for determining a sprinkler water delivery requirement to control a fire. The invention also relates to an apparatus for measuring heat flux, especially in connection with fire protection, the fire testing of materials, and determining a sprinkler water delivery rate.

2. Background of the Invention

The fire hazard represented by storage of a given material is often characterized by the rate of delivered sprinkler water required to suppress or control a fire of that material. The present state-of-the-art for hazard characterization is to perform replicate tests in which: the material is ignited; the fire is allowed to grow until it is sensed by sprinklers; and the sprinklers then activate to deliver water to the fire. The delivered water density, that is, the amount of water delivered by the sprinklers per unit area of the floor, is systematically increased until a delivery rate that controls the fire is found. Many standard tests must be performed with the same material to determine what rate of sprinkler water delivery is required to control the fire from the burning material. These replicate tests consume a great deal of personnel labor and material, and are thus very expensive and time-consuming.

The severity of fires and the hazards they present are assessed in terms of the total chemical heat release rate of the fire and the heat flux emitted. Heat flux is defined as the rate of energy transfer per unit surface area. Heat flux is typically expressed in units of kilowatts per square meter or BTU per square foot per minute. The measurement of heat flux is of importance in many sciences, including the fire testing of many materials. The heat flux emitted by burning materials may ignite, or aid in the burning of, nearby materials. In one known test set up, a gas burner is positioned at the base of and between two parallel panels on which a test material, for example, a fire resistant material such as polyurethane insulation, is placed. Measurement of heat flux in this parallel panel test provides valuable information about the response of the test material to the flames from the burner.

Instrumentation presently available for measuring heat flux requires complex, time-consuming installation, and is not sufficiently robust to withstand repeated use in very severe fire environments. The conventional instrumentation usually consists of water-cooled heat flux gauges that need to be individually installed, for example, directly on the panels bearing the test material. These gauges are exposed to flames during use. Individual heat flux gauges must undergo time-consuming calibration before and after the test because their sensing elements are easily damaged or impacted by fire impingement and by the deposition of soot and other incomplete products of combustion. A measurement uncertainty arises when post-test calibration shows that the gauge calibration constant has shifted as a result of this impact. Moreover, the gauges are individually water-cooled and mounted to view the flames through openings drilled in the material and supporting structure. This adds time and expense to the testing program and severely limits the number of heat flux measurement stations that can be installed. In some fire test configurations, such as commodity classification, it is not practical to install heat flux gauges due to the difficulty of protecting water cooling lines and electrical connections in highly hazardous locations.

SUMMARY OF THE INVENTION

An object of the invention is to provide an inexpensive, easily installed device for measuring heat flux distribution.

Another object of the invention is to provide a simple method for measuring heat flux distribution.

Yet another object of the invention is to provide a durable apparatus for measuring heat flux distribution from gas burners or fire testing apparatuses.

Still another object of the invention is to provide a method for evaluating fire hazards based on measurements of the heat flux in test fires.

Another object of the invention is to provide a method for evaluating the total heat transfer to the burning fuel from spatially distributed heat flux measurements. The total heat transfer is defined as the product of heat flux and the area receiving that heat flux, summed over the entire area receiving heat flux. Total heat transfer is typically expressed in units of kilowatts or BTU/minute.

A further object of the invention is to provide a method for determining the area over which heat is transferred to the material.

Another object of the invention is to provide a method for determining the rate of flow of sprinkler water required to control a fire based on a measurement of the total heat transfer to the burning fuel.

A further object of the inventions is to have a single test that is able to determine the required flow rate of sprinkler water necessary to control a fire for a given material.

The amount of sprinkler water flow rate required to control a fire can be determined by the method of the present invention which includes: measuring the spatial heat flux distribution in a test fire; calculating the effective heat flux received by the material surface, and calculating the sprinkler water delivery rate needed to absorb the heat flux using the energy required to vaporize the delivered water.

The method of the present invention solves the problems of conventional methods by reducing or eliminating the need for multiple and incremental testing. It has been discovered that the sprinkler water delivery rate required for control of the commodity is proportional to the total heat transfer to the fuel (i.e. product of the flame heat flux and flame area) just before the moment when sprinklers sense the fire, causing the sprinkler valve to open and deliver water to the fire. The proportionality constant is easily calculated from the heat of vaporization of water, that is, the rate at which water will be converted to steam per unit of applied heat flux.

By the present invention, the amount of sprinkler water necessary to control the burning of a material can be determined from a single test. The method of the present invention enables an evaluation of the fire hazard of materials based on heat flux measurements. The rate of sprinkler water required to control an array of a burning commodity, such as a commodity in a warehouse, is proportional to the heat flux to the surface of the commodity. The heat flux transferred to the heat flux measurement pipe of the present invention in a free-burning fire is closely related to the water flow rate required to suppress the fire.

Instead of individually installed heat flux gauges fixed to test panels to measure heat flux at various heights in a fire test, the heat flux measurement pipe, or device, of the present invention is a unitary device that has the capability for simultaneous measurements of heat flux along its length. The heat flux measurement pipe of the present invention is extremely stable and rugged, has no moving parts, and is easy to position in a test set up. The heat flux measurement pipe does not need to be connected to the panels bearing the test material. Instead, it can merely be positioned near or between the panels while, for example, being supported on wheeled support.

The heat flux measurement pipe is a water-cooled pipe that makes use of the change in water temperature over a distance along a water passageway, for example, a spiral water passageway, within the pipe. An outer pipe fits tightly over an inner core into which a spiral water passageway is machined. Thermocouples for measuring the temperature of the water in the water passageway are fixed on the core at spaced locations in the water passageway, adjacent thermocouples defining sections of the water passageway between them. At steady-state, the net heat transfer rate to each section of the water passageway can be determined from the product of mass flow rate of water entering or leaving that section and the difference in water temperature between the entrance and exit of that section. Accordingly, only the overall water mass-flow-rate and the water temperature at various locations along the passageway need be measured to determine the spatial distribution of heat transferred to the pipe. The thermocouples measure the temperature of the water at the entrance and exit of each section of the water passageway. By forcing the water to travel in a tight spiral in an annulus between the outer pipe and the core, there is assurance that any spatial non-uniformity will be averaged out, improving heat transfer and resulting in a water temperature that represents the average heat transfer to each pipe section. Heat flux levels can be readily determined from the measured water temperatures and the pipe geometry using known calculations.

The heat flux measurement pipe of the present invention can provide measurements of the heat flux distribution from flames in standard tests to evaluate the fire hazard of typical warehouse commodities and determine the rate of sprinkler water delivery needed to control the fire.

Thus, the use of the heat flux measurement pipe in fires involving test materials measures the spatial distribution of heat flux, and from this the sprinkler water delivery rate that would absorb the heat flux in converting the water to steam can be determined. When the heat flux from the fire is absorbed, the fire will stop spreading and burn out. This method of evaluating fire hazards determines the required sprinkler water delivery rate from heat flux measurements of a single test, rather than from the multiple tests that were heretofore considered necessary.

BRIEF DESCRIPTION OF THE DRAWINGS

One embodiment of the invention is explained in greater detail by way of the drawings, where the same reference numerals refer to the same features.

FIG. 6 is a sketch showing how to determine the effective heat flux and length from the measured vertical and horizontal heat flux distributions shown in FIG. 5.

DETAILED DESCRIPTION OF THE PREFERRED EMBODIMENT

Figure 1:
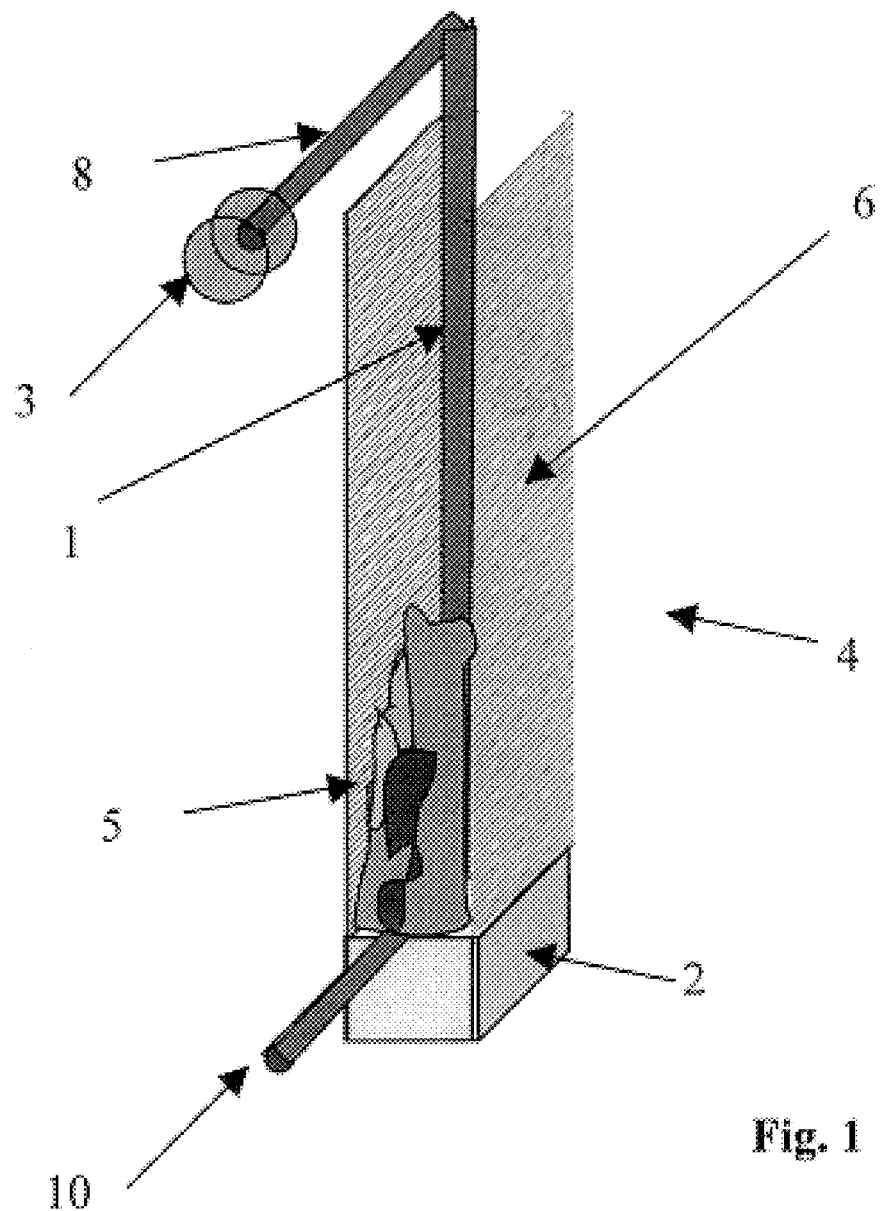
FIG. 1 is a schematic perspective view of a heat flux measurement pipe according to the present invention in position at a fire test set up.

As can be seen from FIG. 1, the heat flux measurement device, or heat flux measurement pipe, according to the present invention, which is designated generally by the reference numeral 1, is designed to be installed within a testing apparatus 4 for testing the flame properties of materials. The heat flux measurement device 1 runs the vertical length of a testing apparatus 4 that includes a gas burner 2 and test panels 6 of material to be tested. Cold water enters the heat flux measurement device 1 through a water flow rate measurement device 3 and an inlet conduit 8 connected to the top of the device, and heated water exits through an outlet conduit 10 connected at the bottom of the device. The product of the water flow rate and the segmental increases in water temperature as water flows through the device 1 indicates the distribution of heat transfer to the device 1 from both the flames 5 being supplied by the gas burner 2 and the panels 6 of the material being tested. From this heat transfer distribution, information about the fire behavioral characteristics of the panels 6 can be obtained.

Figure 2:
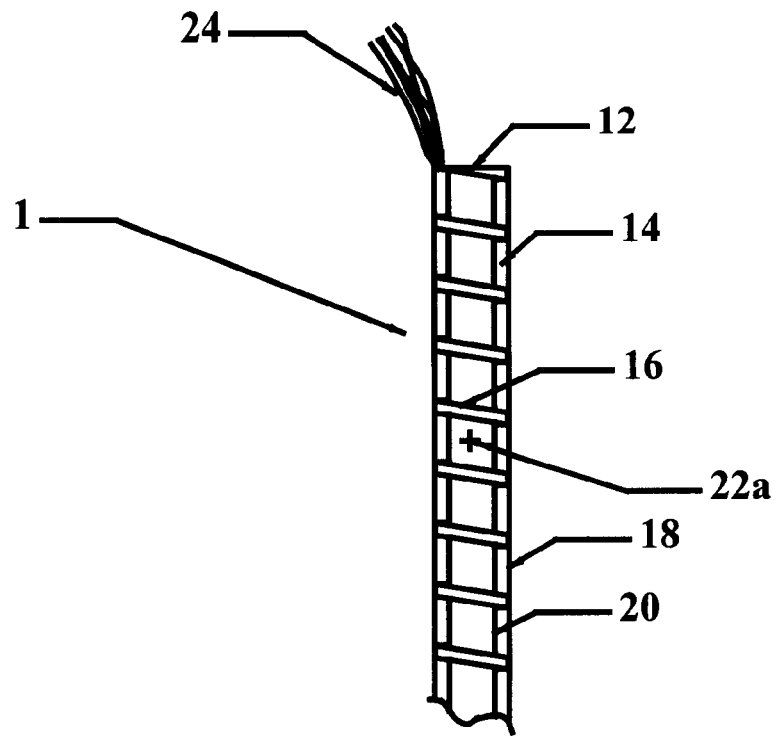
FIG. 2 is a cross section of the heat-flux measurement pipe of FIG. 1 with a portion moved.
Figure 2:
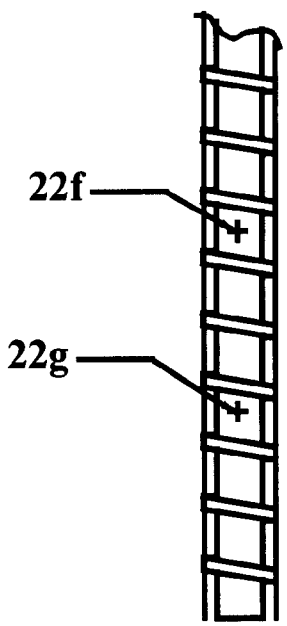

As can be seen from FIG. 2, the heat flux measurement device 1 has a core 12 that can be generally cylindrical and made out of aluminum. The core 12 is machined to form a spiral groove, which defines a reduced-diameter portion 20 and extends the length of the core. The machining leaves on core 12 a helical rib 16 that snugly engages the inside of an outer pipe 18 defining the exterior of a heat flux measurement device 1. The outer pipe 18 can be made of steel. The reduced diameter portion 20 defines a radially inner surface of a spiral water passageway 14. The inlet conduit 8 (FIG. 1) is connected to the top of the passageway 14, and the outlet conduit 10 (FIG. 1) is connected to the bottom of the passageway 14. Typically, the core outer diameter is about 0.74 inches; the distance between convolutions of the rib is about 0.5 inches; the rib 16 is about 0.125 inches wide; and the distance between the inner surface of the outer pipe 18 and the reduced-diameter portion 20 of the core 12 is about 0.135 inches. Thermocouple lead wires 24 are shown extending out the top and bottom of the core. Portions of the lead wires 24 extending through the passageway 14 are not shown.

Figure 3:
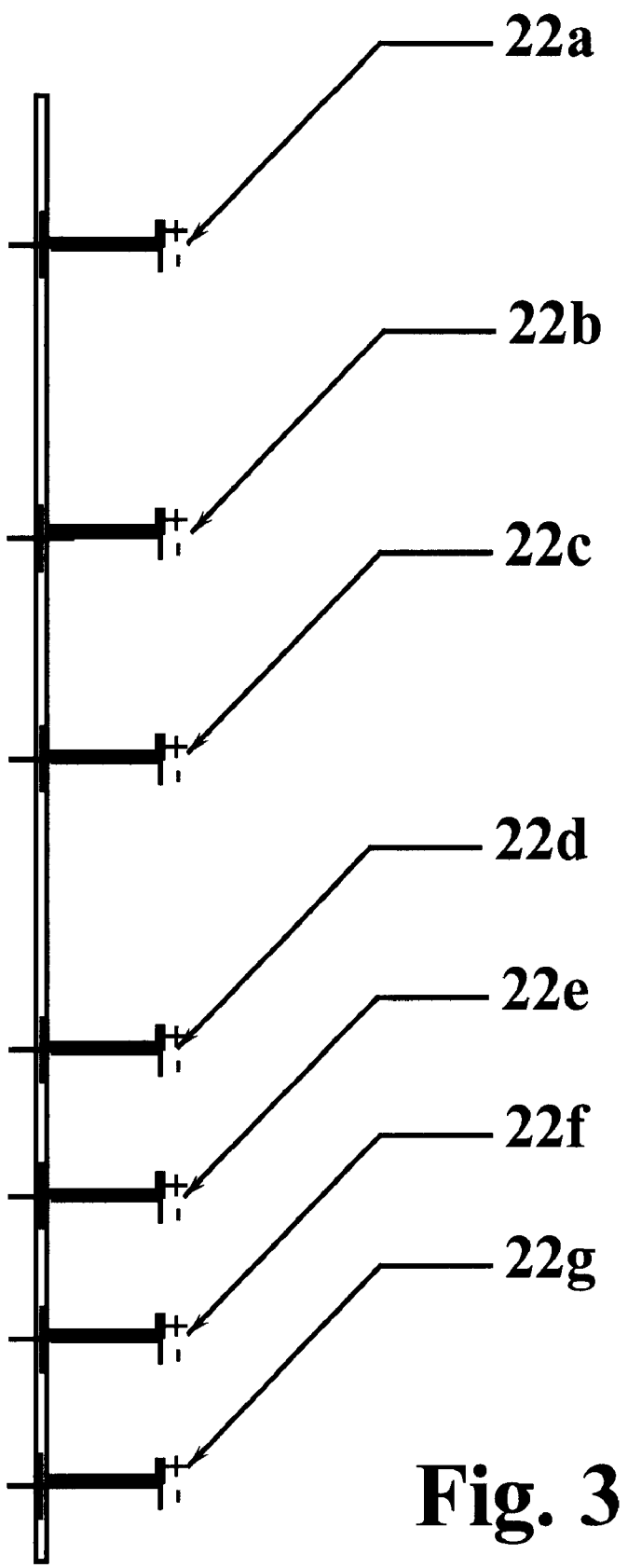
FIG. 3 is a schematic illustration of an arrangement of temperature sensors in the heat-flux measurement pipe of FIG. 1.

As can be seen from FIG. 2, thermocouples 22a-22g are located at spaced positions along the spiral water passageway 14 of the core. A schematic of the thermocouple layout is shown in FIG. 3. The thermocouple leads are threaded helically around the core 12 through the passageway 14 to the exit of the passageway at the bottom of the heat flux measurement device 1 and then to a measurement station where thermocouple differential voltages are measured. Generally, a thermocouple is a sensing element with two dissimilar metallic conductors joined end to end, the junction, when heated, producing a voltage differential between the two conductors. The temperature at the thermocouple lead can be determined from the voltage differential using standard tables. In the present invention, the thermocouples 22a-22g are used to measure the temperatures of the water flowing through the heat flux measurement device 1 at their respective locations. The product of the water flow rate and the temperature difference between adjacent thermocouples determines is the heat gain in the segment of pipe between these thermocouples. Dividing this heat gain by the surface area of the pipe between the adjacent thermocouples gives the local heat flux.

Lead wires 24 from the thermocouples 22a-22g extend upward through the passageway 14 and out at the top of the device 1. For this purpose, a port can be formed adjacent to the inlet of the passageway 14, through the top of the inner core 12, with the lead wires extending through an elastomeric plug in the port in a watertight manner. Alternative arrangements for extending the lead wires 24 out of the device can be made. In the illustrated embodiment, lead wires 24 to each of the thermocouples 22a-22g extend down from the top of the heat flux measurement pipe device 1 through the spiral water passageway 14. The lead wires to the various thermocouples 22a-22g have different lengths so as to suspend the junctions of the thermocouples at various positions in the spiral passageway 14, the junctions being spaced axially from one another along the axis of the heat flux measurement device 1. The heat flux measurement device 1 has the seven thermocouples 22a-22g spaced at distances of 0.5, 1.5, 2.5, 3.5, 5.5, 7, and 9 feet, respectively, measured from the bottom. This spacing provides greater resolution in the region of the fire. The thermocouples 22a, 22f, and 22g are shown in FIG. 2 in exemplary positions along the spiral passageways 14. The other thermocouples are not shown in FIG. 2. Other spacing arrangements can also be useful. The thermocouples 22a-22g can be ungrounded junction chromel-alumel thermocouples. The ends of the lead wires 24 opposite to the junctions of the thermocouples 22a-22g are connected to devices for recording the temperatures and/or calculating heat fluxes in accordance with known formulas.

The water flow rate through the pipe is measured by an electronic flowmeter 3 (shown in FIG. 1), such as the +GF+Signet 8511 Micro Flow Sensor. This device is mounted on the water inlet 8 to the heat flux measurement device 1 as is shown in FIG. 1. Leads (not shown) from the flowmeter are routed to the instrumentation station, where thermocouple signals and water flow rates are simultaneously recorded. The heat flux to a section of the heat flux measurement device 1 is the product of the water flow rate, the specific heat of water (expressed in units such as joules per gram degree C or BTU per pound degree F) and the difference in water temperature entering and exiting the section, respectively, divided by the exterior surface area of this section of the pipe. The seven thermocouple locations in the embodiment shown in FIG. 1 thus provide six heat flux measurements at distances along the pipe corresponding to the midpoints between pairs of adjacent thermocouples. The respective heat fluxes are measured simultaneously with a computer-based data acquisition system Calibration of this device requires only an initial calibration of the water flow measuring device 3 and a minor correction for differences in thermocouple offset voltages, which is easily deduced from pre-test heat flux measurements.

The heat flux measurement device 1 has a small diameter so that it does not disturb the fire or the airflow near the fire, thus ensuring that the device itself does not alter the measurement of flame heat flux. The diameter of the annulus and the flow rate of water are chosen to: (1) ensure efficient heat transfer from the pipe to the water-immersed thermocouples; (2) ensure that temperature differences between thermocouples are large enough to be accurately measured, but not so large as to cause boiling before the water exits the pipe; (3) ensure that the heat flux measurement will be responsive to transient fire behavior; and (4) ensure a reasonable water pressure drop across the pipe.

The heat flux measurement device 1 is manufactured to be a rugged instrument that is easy to install and calibrate, thus dramatically reducing the time and effort involved in installation in fire test configurations. It be easily positioned in most existing large-scale standard fire tests. The device 1 is water-cooled and highly durable, having no sensing elements that are exposed to flames.

Figure 4:
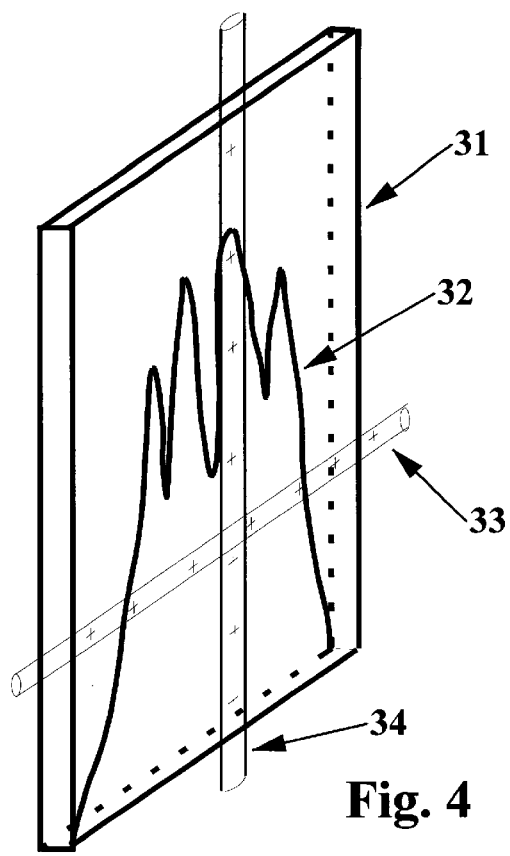
FIG. 4 is a schematic illustration of a fire test set up employing heat flux measurement pipes according to the present invention.
Figure 5:
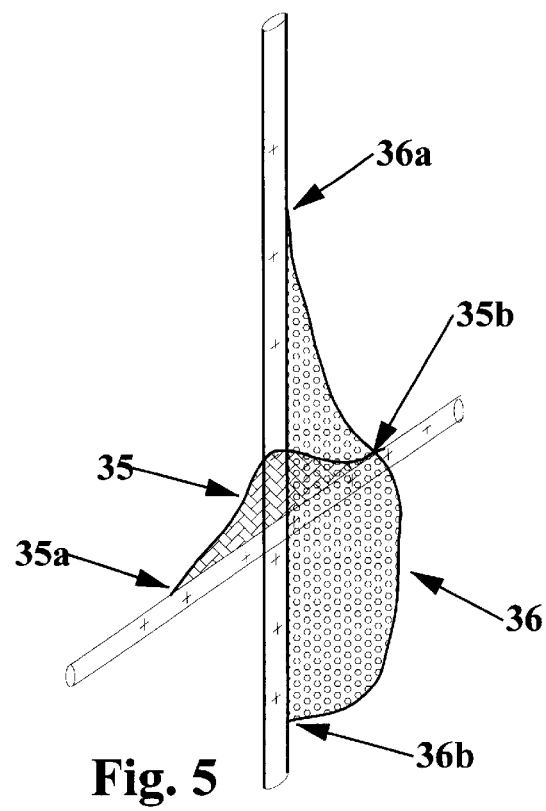
FIG. 5 is a graphical representation of the vertical and horizontal distribution of heat flux of the fire in the fire test set up of FIG. 4.

FIG. 4, FIG. 5 and FIG. 6 illustrate a measurement of both the spatial extent of heat flux from a fire and the evaluation of the total heat transfer to the test material, by using the method according to the present invention. In FIG. 4, a test material 31 is mounted in a wall configuration and ignited, followed by flame spread on the wall surface, 32. Heat pipes 33 and 34 adjacent to the wall provide the horizontal 35 and vertical 36 distributions of the heat flux from the fire as is illustrated by FIG. 5. Alternatively, the method of the present invention can be carried out by using linear arrays of heat-flux-gauges-instead of the heat pipes 33 and 34. The area under each curve represents the integral of the heat flux with respect to distance along the horizontal 33 or vertical 34 heat pipe. The total heat transfer to a burning commodity is calculated by integrating in both the horizontal and vertical directions. The heat flux measurements also indicate the spatial extent of the fire, horizontally 35a-35b, and vertically, 36a-36b, from which the burning surface area is inferred.

In order to simplify the calculation of the total heat transfer to the test material, the measured horizontal or vertical distributions of heat flux is replaced with an effective heat flux and effective width (or height). FIG. 6 shows how to calculate the effective heat flux, $q_0$, and the effective width, l, from a measured heat flux distribution. The effective heat flux, $q_0$, and the effective width, l, of the heat flux can be determined by first setting $$lq_0 = \int_{\infty}^{\infty} f(x)dx$$

and then choosing $q_0$ and l that minimize the integral $$B = \int_{\infty}^{\infty} [f(x) - q(x)]^2 dx$$

Here f(x) is the measured variation in heat flux with distance, x and q(x) is the variation in the effective heat flux $q_0$ with distance $q(x)=q_0$ over the width (or height), l, and is equal to zero outside this width (or height). The procedure can apply to either the vertical or horizontal distributions.

The density of water per unit material surface area, $m_w''$, needed to absorb the heat flux, $q_0$, is equal to $q_0/L$, where L is the heat required to vaporize a unit mass of the sprinkler water. Fire protection engineers express the required sprinkler water flow rate, D, in terms of the sprinkler water flow rate per unit floor area, in units of mm/minute or gallons per square foot per minute. To calculate D, the amount of exposed material surface area per unit floor area is required. Thus, let $a_f$ be the ratio of the material surface area divided by the associated floor surface area. In a fire test configuration comprising vertical and horizontal material surfaces, one is usually most concerned with the vertical surfaces. Using this definition, the sprinkler water flow rate that is needed to control the fire is $$D = \dot{m}_w'' a_f = \frac{q_0 a_f}{L}$$

where $a_f$ is the area of the exposed material per unit floor area. It is assumed here that the sprinkler water can reach most of the exposed test material surface area. In addition, it is assumed that the water is applied soon enough for it to reach the burning surface without being blown away by the rising fire plume from a fire that has grown to become very large.

Test materials are often classified in terms of their relative fire hazard, or the sprinkler water flow rate per unit surface area required to control the fire at the moment when sprinklers might sense the fire and activate.

Although the invention is described in detail with respect to a preferred embodiment, it will now be apparent from the foregoing to those skilled in the art that changes and modifications may be made without departing from the invention in its broader aspects, and the invention, therefore, as defined in the claims is intended to cover all such changes and modifications as fall within the true spirit of the invention.

What is claimed is:

1. A method of determining a sprinkler water flow rate from at least one sprinkler required to control a fire comprising:

measuring spatial heat flux distribution to a burning material in a test fire;

calculating the effective heat flux, $q_0$, to the burning material; and calculating a sprinkler water delivery rate per unit exposed material area, $m_w''=q_0/L$, required to absorb the heat transfer through a vaporization of water, wherein L is the heat required to vaporize a unit mass of water.

2. The method of claim 1, wherein the method further comprised estimating a sprinkler water flow rate per unit floor area, $D=m_w''a_f=q_0a_f/L$, required to control a fire of the material, wherein $a_f$ is the area of exposed material per unit floor area.

3. The method of claim 1, wherein said step of measuring the heat flux distribution comprises measuring the flow rate of a fluid flowing through a passageway of an elongated element; and measuring the temperature of the fluid at points along the passageway spaced longitudinally from one another with respect to the passageway.

4. The method of claim 3, wherein the step of measuring the flow rate comprises measuring the flow rate through a spiral passageway between an outer pipe and an inner core within the outer pipe.

5. The method of claim 3, wherein the step of measuring the temperature comprises extending lead wires with temperature-sensing elements longitudinally through the passageway to the top of the elongated element.

6. The method of claim 3, wherein the step of measuring the flow rate comprises measuring the flow rate of a fluid flowing through a spiral passageway extending axially within the elongated element.

7. The method of claimed 3, wherein said step of measuring the flow rate comprises measuring the flow rate through a spiral passageway defined at least in part by a helical rib on an inner pipe within an outer pipe.

8. The method of claim 7, wherein the step of measuring the flow rate comprises measuring the flow rate through a passageway defined at least in part by an outer pipe having a diameter of less than 1.0 inches.

9. The method of claim 7, wherein the step of measuring the temperature comprises extending lead wires of temperature-sensing elements longitudinally through the passageway to the top of the elongated element.

* * * * *